United States Patent
Luemmen et al.

(10) Patent No.: US 7,994,334 B2
(45) Date of Patent: Aug. 9, 2011

(54) FUNGICIDE PYRIDINYLOXY SUBSTITUTED PHENYLAMIDINE DERIVATIVES

(75) Inventors: Peter Luemmen, Idstein (DE); Klaus Kunz, Düsseldorf (DE); Jörg Greul, Leichlingen (DE); Oliver Guth, Leverkusen (DE); Benoît Hartmann, Sainte Foy-lès-Lyon (FR); Kerstin Ilg, Köln (DE); Wahed Ahmed Moradi, Monheim an Rhein (DE); Thomas Seitz, Langenfeld (DE); Jean-Pierre Vors, Sainte Foy lès Lyon (FR); Peter Dahmen, Neuss (DE); Arnd Voerste, Köln (DE); Ulrike Wachendorff-Neumann, Neuwied (DE); Mark Drewes, Langenfeld (DE); Ralf Dunkel, Lyons (FR); Ronald Ebbert, Nürnberg (DE); Peter Lösel, Leverkusen-Hitdorf (DE); Olga Malsam, Rösrath (DE)

(73) Assignee: Bayer Cropscience AG, Monheim (DE)

( * ) Notice: Subject to any disclaimer, the term of this patent is extended or adjusted under 35 U.S.C. 154(b) by 631 days.

(21) Appl. No.: 12/063,667

(22) PCT Filed: Sep. 12, 2006

(86) PCT No.: PCT/EP2006/066290
§ 371 (c)(1),
(2), (4) Date: Feb. 12, 2008

(87) PCT Pub. No.: WO2007/031523
PCT Pub. Date: Mar. 22, 2007

(65) Prior Publication Data
US 2008/0255208 A1    Oct. 16, 2008

(30) Foreign Application Priority Data
Sep. 13, 2005   (EP) .................................. 05356156

(51) Int. Cl.
*C07D 211/72* (2006.01)
*A01N 25/26* (2006.01)

(52) U.S. Cl. ....................................... 546/300; 504/100
(58) Field of Classification Search .................. 546/300; 514/351; 504/100
See application file for complete search history.

(56) References Cited

U.S. PATENT DOCUMENTS

| 3,898,277 A | 8/1975 | Duerr et al. |
| 5,064,846 A | 11/1991 | Broadhurst |
| 2003/0008884 A1 | 1/2003 | Gerusz et al. |
| 2010/0093534 A1* | 4/2010 | Kunz et al. ................... 504/100 |
| 2010/0113276 A1* | 5/2010 | Kuhn et al. ................... 504/242 |

FOREIGN PATENT DOCUMENTS

| EP | 1178038 | 2/2002 |
| EP | 1178039 | 2/2002 |
| EP | 1179528 | 2/2002 |
| EP | 1570736 | 9/2005 |
| JP | 63250371 | 10/1988 |
| WO | WO 00/46184 | 8/2000 |

OTHER PUBLICATIONS

J.W. Liebeschuetz et al., "Rationally Designed Guanidine and Amidine Fungicides", *Pesticidal Science*, vol. 50:258-274; 1997.
International Search Report No. PCT/EP2006/066290, dated Nov. 24, 2006, 3 pgs.

* cited by examiner

*Primary Examiner* — Janet L. Andres
*Assistant Examiner* — John Mabry
(74) *Attorney, Agent, or Firm* — Baker Donelson Bearman, Caldwell & Berkowitz, PC

(57) ABSTRACT

The present invention relates to 2,5-di-substituted-4-pyridinyloxy-substituted-phenyl-amidine derivatives, notably to 2,5-dialkyl-4-pyridinyloxy-substituted-phenyl-amidine derivatives, of formula (I) in which the substituents are as in the description, their process of preparation, their use as fungicide active agents, particularly in the form of fungicide compositions, and methods for the control of phytopathogenic fungi, notably of plants, using these compounds or compositions (I).

13 Claims, No Drawings

FUNGICIDE PYRIDINYLOXY SUBSTITUTED PHENYLAMIDINE DERIVATIVES

CROSS REFERENCE TO RELATED APPLICATIONS

This is a §371 National Stage Application of International Application No. PCT/EP2006/066290 filed Sep. 12, 2006, which claims priority from European Application No. 05356156.9 filed Sep. 13, 2005.

BACKGROUND OF THE INVENTION

1. Field of the Invention

The present invention relates to 2,5-di-substituted-4-pyridinyloxy-substituted-phenyl-amidine derivatives, notably to 2,5-dialkyl-4-pyridinyloxy-substituted-phenyl-amidine derivatives, their process of preparation, their use as fungicide active agents, particularly in the form of fungicide compositions, and methods for the control of phytopathogenic fungi, notably of plants, using these compounds or compositions.

2. Description of Related Art

In international patent application WO-00/46184 certain phenyl-amidine derivatives are disclosed. However, this document does not specifically disclose nor suggest to select such compounds wherein the phenyl ring is substituted according to the invention thus allowing an unexpected and significantly higher fungicide activity.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining an effectiveness at least equivalent to the already known compounds.

We have now found a new family of compounds which possess the above mentioned effects or advantages.

SUMMARY OF THE INVENTION

Accordingly, the present invention provides 2,5-di-substituted-4-pyridinyloxy-substituted-phenyl-amidine derivatives of formula (I):

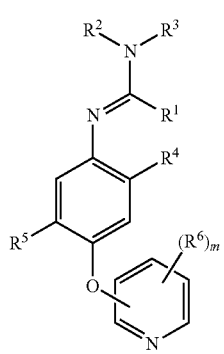

(I)

wherein $R^1$ represents H, a substituted or non substituted $C_1$-$C_{12}$-alkyl, a substituted or non substituted $C_2$-$C_{12}$-alkenyl, a substituted or non substituted $C_2$-$C_{12}$alkynyl, SH or a substituted or non substituted S—$C_1$-$C_{12}$-alkyl;

$R^2$ represents a substituted or non substituted $C_1$-$C_{12}$-alkyl;

$R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or $R^1$ and $R^2$, $R^1$ and $R^3$ or $R^2$ and $R^3$ can form together a substituted or non substituted 5 to 7-membered heterocycle;

$R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;

$R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;

m represents 1, 2, 3 or 4;

$R^6$ represents H, halogen, cyano, substituted or non substituted phenoxy, substituted or non substituted phenyl, substituted or non substituted $C_1$-$C_{12}$-alkyl, or halogeno-$C_1$-$C_{12}$-alkyl, $NR^7R^8$, $OR^7$, $SR^7$, trialkysilyl, $COOR^7$, $C(R^7)$=$NOR^8$;

$R^7$, $R^8$ represent H, substituted or non substituted $C_1$-$C_{12}$-alkyl, aryl;

$R^7$ and $R^8$ may form a substituted or non substituted, saturated or non saturated 5 to 7-membered heterocycle;

as well as salts; N-oxydes, metallic complexes, metalloidic complexes and optically active or geometric isomers thereof.

DETAILED DESCRIPTION OF A PREFERRED EMBODIMENT

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulphur.

Preferred compounds of formula (I) according to the invention are those wherein $R^1$ represents H; $C_1$-$C_{12}$-alkyl, preferably $C_1$-$C_{12}$-alkyl like methyl and ethyl; or SH.

Other preferred compounds of formula (I) according to the invention are those wherein $R^2$ represents methyl or ethyl.

Still other preferred compounds of formula (I) according to the invention are those wherein $R^3$ represents $C_2$-$C_{12}$-alkyl, preferably a non substituted $C_2$-$C_4$-alkyl like ethyl, n-propyl, i-propyl; $C_2$-$C_{12}$-alkenyl, preferably $C_3$-$C_4$-alkenyl like propenyl or allyl; $C_3$-$C_6$-cycloalkyl like cyclopropyl.

Still other preferred compounds of formula (I) according to the invention are those wherein $R^2$ and $R^3$ can form together a substituted or non substituted 5 to 7-membered heterocycle, preferably a 6-membered heterocycle, more preferably a pipiridinyl or a pyrrolidinyl, even more preferably a bis-alkylated-pyrrolidinyl like a bis-methyl-pyrrolidinyl.

Still other preferred compounds of formula (I) according to the invention are those wherein $R^4$ represents a $C_1$-$C_{12}$-alkyl, preferably a non substituted $C_1$-$C_{12}$-alkyl like methyl and ethyl; a halogen atom like a chlorine atom.

Still other preferred compounds of formula (I) according to the invention are those wherein $R^5$ represents a $C_1$-$C_{12}$-alkyl, preferably a non substituted $C_1$-$C_{12}$-alkyl like methyl and ethyl; a halogen atom like a chlorine atom.

Still other preferred compounds of formula (I) according to the invention are those wherein $R^6$ represents H, halogen, cyano, substituted or non substituted $C_1$-$C_{12}$-alkyl, or halogeno-$C_1$-$C_{12}$-alkyl, $NR^7R^8$, $OR^7$, $SR^7$, $COOR^7$.

Still other preferred compounds of formula (I) according to the invention are those wherein $R^7$ or $R^8$ independently represent H, methyl, ethyl, aryl preferably substituted phenyl or may form a substituted or non substituted, saturated or non saturated 5- to 7-membered heterocycle, preferably piperidinyl or morpholinyl.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combine:

preferred features of $R^1$ with preferred features of $R^2$ to $R^8$;
preferred features of $R^2$ with preferred features of $R^1$ to $R^8$;
preferred features of $R^3$ with preferred features of $R^1$ to $R^8$;
preferred features of $R^4$ with preferred features of $R^1$ to $R^8$;
preferred features of $R^5$ with preferred features of $R^1$ to $R^8$;
preferred features of $R^6$ with preferred features of $R^1$ to $R^8$;
preferred features of $R^7$ with preferred features of $R^1$ to $R^8$.

In these combinations of preferred features of the substituents of the compounds according to the invention, the said preferred features can also be selected among the more preferred features of each of $R^1$ to $R^6$ so as to form most preferred subclasses of compounds according to the invention.

The present invention also relates to a process for the preparation of compounds of formula (I). Generally, the preparation of compound of formula (I) according to the invention can be carried out as illustrated by scheme 1.

Scheme 1

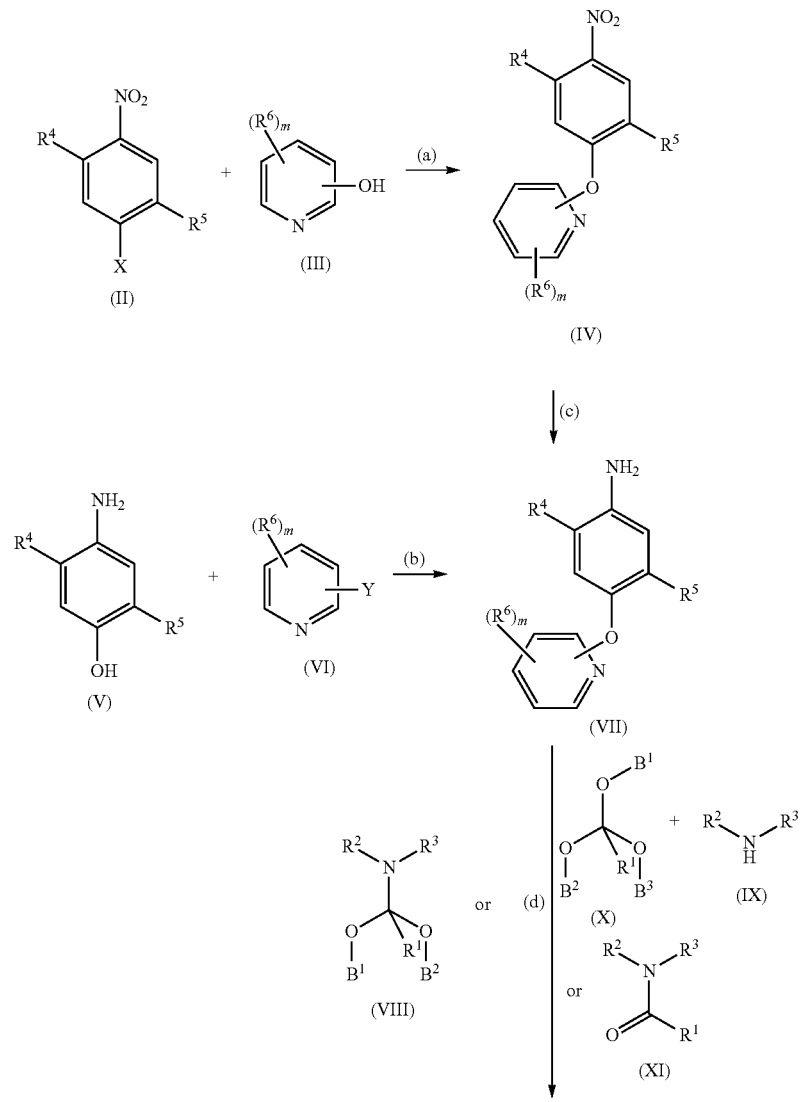

-continued

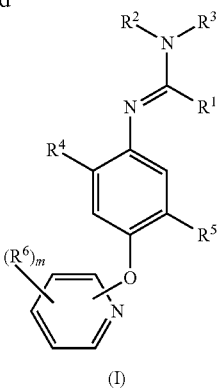

(I)

Nitrophenylether derivatives of formula (IV) can be obtained according to process (a) by reacting nitrobenzene derivatives of formula (II)

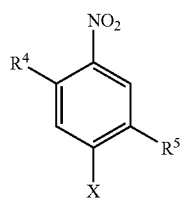

(II)

wherein
R$^4$ and R$^5$ are as herein-defined;
X represents halogen, triflate, SOMe, mesylate or tosylate;
with hydroxypyridine derivatives of formula (III)

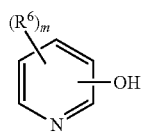

(III)

wherein
R$^6$ and m are as herein-defined.
Process (a) according to the invention can further comprise one or more of the following characteristics:
  presence of a base;
  presence of a diluent;
  presence of a catalyst.
Aniline derivatives of formula (VII) can be obtained according to process (b) by reacting aniline derivatives of formula (V)

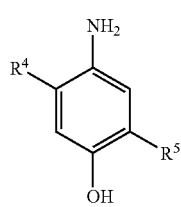

(V)

wherein
R$^4$ and R$^5$ are as herein-defined;
with pyridine derivatives of formula (VI)

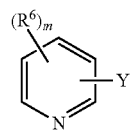

(VI)

wherein
R$^6$ and m as herein-defined;
Y represents halogen, triflate, SOMe, mesylate or tosylate.
Process (b) according to the invention can further comprise one or more of the following characteristics:
  presence of a base;
  presence of a diluent;
  presence of a catalyst.
Process (b) is then followed by (c) the reduction of nitrophenylether derivatives of formula (IV). Preferably, the reduction reaction is carried out in presence of stannous chloride in concentrated hydrochloric acid.
Amidine derivatives of formula (I) can be obtained according to process (d) by reacting aniline derivatives of formula (VII)

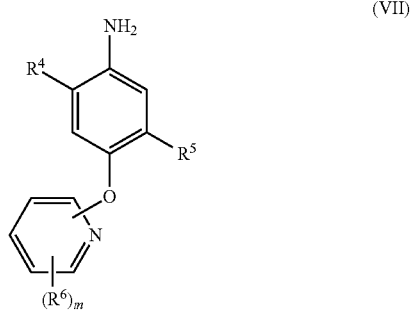

(VII)

wherein R$^4$, R$^5$, R$^6$ and m are as defined above.
Various alternatives of process (d) according to the invention can be considered, they are defined as process (d1), process (d2) and process (d3) according to the invention.
Process (d) according to the invention comprises reacting aniline derivatives of formulae (VII) with different reagents thus defining processes (d1), (d2) and (d3) respectively Process (d1) is carried out further using amino-acetal derivatives of formula (VIII)

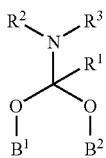

(VIII)

wherein
$R^1$, $R^2$, $R^3$ are as herein-defined;
$B^1$ and $B^2$ represent each alkyl or together cycloalkyl.

Process (d1) according to the invention can further comprise one or more of the following characteristics:
 presence of an acid or a base;
 presence of a diluent.

Process (d2) is carried out further using amine derivatives of formula (IX)

(IX)

wherein $R^2$ and $R^3$ are as herein-defined; in the presence of orthoester derivatives of formula (X)

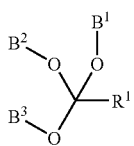

(X)

wherein
$R^1$ is as herein-defined;
$B^1$, $B^2$ and $B^3$ represent each alkyl.

Process (d3) is carried out further using amide derivatives of formula (XI)

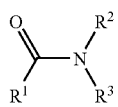

(XI)

wherein $R^1$, $R^2$, $R^3$ are as herein-defined.

Process (d3) according to the invention can further comprise one or more of the following characteristics:
 presence of a halogenation agent, like $PCl_5$, $PCl_3$, $POCl_3$, $SOCl_2$;
 presence of a diluent.

Suitable diluents for carrying out the processes (a), (b) and (c) according to the invention are all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Suitable diluents for carrying out the processes (d1), (d2) and (d3) according to the invention are in each case all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethyl-acetamide, N-methylformanilide, N-methylpyrrolidone or hexamethylphosphoric triamide; esters, such as methyl acetate or ethyl acetate; sulphoxides, such as dimethylsulphoxide; or sulphones, such as sulpholane; alcohols, such as methanol, ethanol, n- or iso-propanol, n-, iso-, sec- or tert-butanol, ethanediol, propane-1,2-diol, ethoxyethanol, methoxyethanol, diethyleneglycolmonomethylether, diethyleneglycolmonoethylether; mixtures thereof with water or pure water.

Suitable acid binders for carrying out the processes (a), (b) and (c) according to the invention are all inorganic and organic bases customary for such reactions. Preference is given to using alkaline earth metal or alkali metal hydrides, hydroxides, amides, alcoholates, acetates, carbonates or hydrogen carbonates, such as sodium hydride, sodium amide, lithiium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, or ammonium carbonate; and also tertiary amines, such as trimethylamine, triethylamine, tributylamine, N,N-dimethylaniline, N,N-dimethyl-benzylamine pyridine, N-methylpiperidine, N-methylmorpholine, N,N-dimethylaminopyridine, diazabicyclooctane (DABCO), diazabicyclononene (DBN) or di-azabicycloundecene (DBU).

Suitable acid binders for carrying out the processes (b), (c), (d) according to the invention are in each case all inorganic and organic bases customary for such reactions. Preference is given to using alkaline earth metal or alkali metal hydrides, hydroxides, amides, alcoholates, acetates, fluorides, phosphates, carbonates or hydrogen carbonates, such as sodium hydride, sodium-amide, lithium diisopropylamide, sodium methanolate, sodium ethanolate, potassium tert-butanolate, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate or caesium carbonate; and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

Suitable acids for carrying out the process (d1) according to the invention are all inorganic and organic acids customary for such reactions. Preference is given to using para-toluene sulfonic acid, methane sulfonic acid, hydrochloric acid (gas, aqueous or organic solution) or sulphuric acid.

Suitable condensing agents for carrying out the process (d3) according to the invention are all condensing agents customary for such amidation reactions. Preference is given to using acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclo-hexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane or bromo-tripyrrolidino-phosphonium-hexafluorophosphate.

Compounds of formula (I) according to the invention can be prepared according to the herein described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide composition comprising, as an active ingredient, an effective amount of a compound of formula (I) as hereindefined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilizers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example
as CI-respiration inhibitor like diflumetorim;
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defence like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrroInitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethylcyclohexyl)-3-formylamino-2-hydroxy-benzamide, 2-[[[[1-[3(1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant. Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the invention, mention may be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;

Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;

Leafspot, leaf blotch and leaf blight diseases such as:
*Alternaria* diseases, caused for example by *Alternafia solani*;
*Cercospora* diseases, caused for example by *Cercospora beticola*;
*Cladiosporum* diseases, caused for example by *Cladiosporium cucumerinum*;

*Cochliobolus* diseases, caused for example by *Cochliobolus sativus*;
*Colletotrichum* diseases, caused for example by *Colletotrichum lindemuthianum*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;

Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;

Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;

Smut and bunt diseases such as:
*Sphacelotheca* diseases, caused for example by *Sphacelotheca reiliana*;

*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Fusarium* diseases, caused for example by *Fusarium culmorum*;
*Phytophthora* diseases, caused for example by *Phytophthora cactorum*;
*Pythium* diseases, caused for example by *Pythium ultimum*;
*Rhizoctonia* diseases, caused for example by *Rhizoctonia solani*;
*Sclerotium* diseases, caused for example by *Sclerotium rolfsii*;
*Microdochium* diseases, caused for example by *Microdochium nivale*;
Canker, broom and dieback diseases such as:
*Nectria* diseases, caused for example by *Nectria galligena*;
Blight diseases such as:
*Monilinia* diseases, caused for example by *Monilinia laxa*;
Leaf blister or leaf curl diseases such as:
*Taphrina* diseases, caused for example by *Taphrina deformans*;
Decline diseases of wooden plants such as
Esca diseases, caused for example by *Phaemoniella clamydospora*;
*Eutypa* dyeback, caused for example by *Eutypa lata*;
Dutch elm disease, caused for example by *Ceratocystsc ulmi*;
Diseases of flowers and Seeds such as:
*Botrytis* diseases, caused for example by *Botrytis cinerea*;
Diseases of tubers such as
*Rhizoctonia* diseases, caused for example by *Rhizoctonia solani*.

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following tables of compounds and examples. The following tables illustrate in a non-limiting manner examples of compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

Preparation Example 1

N-Ethyl-N-methyl-N'-[4-(2-chlor-4-trifluormethylpyridyl-6-oxy)-2,5-xylyl]form-amidine—compound of formula (I)

0.25 g (0.79 mmol) of 4-(2-chlor-4-trifluormethylpyridyl-6-oxy)-2,5-xylidine were dissolved in 10 ml of methanol and treated with 0.25 g of a solution of N-ethyl-N-methylformamiddimethylacetal in methanol (60%). The reaction mixture was stirred at 45° C. for 12 h before the solvent was removed in vacuo to yield 200 mg (60% yield, 92% purity) of product; log P (pH 2.3)=2.39 $^1$H NMR δ(ppm) 1.01 (t, $^3J_{HH}$=7 Hz, 3H, CH$_3$), 1.92 (s, 3H, CH$_3$), 2.02 (s, 3H, CH$_3$), 3.21 (s, 3H, NCH$_3$), 4.01 (q, $^3J_{HH}$=7 Hz, 2H, NCH$_2$), 6.71 (s, 1H, aryl-H), 6.86 (s, 1H, aryl-H), 7.29 (s, 1H, aryl-H), 7.61 (s, 1H, aryl-H), 7.65 (b, 1H, amidine-H).

Preparation of Starting Material 4-(2-chlor-4-trifluormethylpyridyl-6-oxy)-2,5-xylidine—compound of formula (VII)

1.76 g (12.86 mmol) of 4-amino-2,5-dimethylphenol, 2.50 g (11.56 mmol) of 2,6-dichloro-4-trifluoromethylpyridine and 1.95 g (14.14 mmol) of potassium carbonate were suspended in 50 ml of DMSO under argon atmosphere. The reaction mixture was stirred at 120° C. for 6 h, cooled down to room temperature, treated with 150 ml of water and 50 ml of a 2N solution of sodium hydroxide in water and extracted with dichloromethane (2×100 ml). The combined organic extracts were dried (MgSO$_4$), filtered and evaporated to dryness. The crude product was purified by silica gel chromatography eluting with cyclohexane/ethyl acetate to yield the title compound in 64% yield (2.6 g, 92% purity); log P (pH 2.3)= 2.77. $^1$H NMR δ(ppm) 1.92 (s, 3H, CH$_3$), 2.02 (s, 3H, CH$_3$), 4.73 (s, 2H, NH$_2$), 6.52 (s, 1H, aryl-H), 6.70 (s, 1H, aryl-H), 7.20 (s, 1H, aryl-H), 7.58 (s, 1H, aryl-H).

TABLE 1

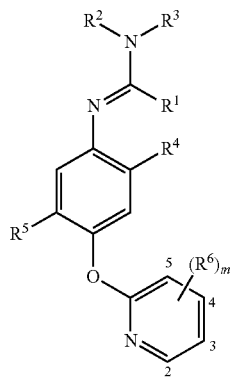

| example | R$^1$ | R$^2$ | R$^3$ | R$^4$ | R$^5$ | R$^6$ | | logP$_a$ |
|---|---|---|---|---|---|---|---|---|
| 2 | H | Me | Et | Me | H | 3-CF$_3$ | 5-Cl | 2.21 |
| 3 | H | Me | Et | Me | H | | 4-Cl | 1.50 |
| 4 | H | Me | Et | Me | H | 2-Cl | 4-CF$_3$ | 2.20 |
| 5 | H | Me | Et | Me | H | | 3-Cl | 1.58 |
| 6 | H | Me | Et | Me | Me | 2-Cl | 3-CF$_3$ | 2.36 |
| 7 | H | Me | iPr | Me | H | 2-Cl | 4-CF$_3$ | 2.22 |
| 8 | H | Me | Et | Me | Me | | 3-Cl | 1.84 |
| 9 | H | Me | Et | Me | H | | 3-CF$_3$ | 1.79 |
| 10 | H | Me | Et | Me | Me | | 3-CF$_3$ | 1.86 |
| 11 | H | Me | Et | Me | Me | 2-Cl | 3-CF$_3$ | 2.11 |
| 12 | H | Me | iPr | Me | Me | 2-Cl | 4-CF$_3$ | 2.52 |
| 13 | H | Me | iPr | Me | Me | 2-Cl | 3-CF$_3$ | 2.51 |
| 14 | H | Me | Et | Me | Me | | 3-I | 2.10 |
| 15 | H | Me | Et | Me | Me | 3-Me | 4-(2-Cl-Ph) | 2.58 |
| 16 | H | Me | Et | Me | H | 3-Me | 4-(2-Cl-Ph) | 2.39 |
| 17 | H | Me | Et | Me | H | | 3-I | 1.87 |
| 18 | H | Et | Et | Me | Me | 2-Cl | 4-CF$_3$ | 2.59 |
| 19 | H | Me | nPr | Me | Me | 2-Cl | 4-CF$_3$ | 2.66 |
| 20 | H | Me | iPr | Me | tBu | 2-Cl | 4-CF$_3$ | 3.17 |
| 21 | H | Me | iPr | Me | iPr | 2-Cl | 4-CF$_3$ | 2.97 |
| 22 | H | Me | Et | Me | tBu | 2-Cl | 4-CF$_3$ | 2.83 |
| 23 | H | Me | Et | Me | Me | 2-Me | 4-Cl | 1.58 |
| 24 | H | Me | Et | Me | iPr | 2-Cl | 4-CF$_3$ | 2.87 |
| 25 | H | Me | Et | Me | Me | 2-Me | 4-CF$_3$ | 2.19 |
| 26 | H | Me | Et | Me | Me | | 2-Cl | 1.78 |
| 27 | H | Me | Et | Me | Me | | 4-CF$_3$ | 1.96 |
| 28 | H | Me | Et | Me | Me | 3-Cl | 5-Cl | 2.00 |
| 29 | H | Me | nPr | Me | Me | 3-Cl | 5-Cl | 2.22 |
| 30 | H | Me | Et | Me | Me | 2-nPr | 4-nPr | 2.97 |
| 31 | H | Me | Et | Me | Me | | 4-CN | 1.42 |
| 32 | H | Me | iPr | Me | Me | 3-Cl | 5-Cl | 2.24 |
| 33 | H | Me | Et | Me | Me | 2-iPr | 4-Cl | 2.18 |
| 34 | H | Me | iPr | Me | Me | 2-iPr | 4-Cl | 2.34 |
| 35 | H | Me | Et | Me | Me | | 3-CN | 1.47 |
| 36 | H | Me | nPr | Me | Me | | 3-CN | 1.63 |
| 37 | H | Me | Allyl | Me | Me | | 3-CN | 1.56 |
| 38 | H | —(CH$_2$)$_5$— | | Me | Me | | 3-CN | 1.58 |
| 39 | H | —(CH$_2$)$_4$— | | Me | Me | | 3-CN | 1.46 |
| 40 | H | —(CH$_2$)$_5$— | | Me | Me | 2-Et | 4-Cl | 2.04 |
| 41 | H | —(CH$_2$)$_4$— | | Me | Me | 2-Et | 4-Cl | 1.95 |
| 42 | H | Me | nPr | Me | Me | 2-Et | 4-Cl | 2.00 |
| 43 | H | Me | iPr | Me | Me | 3-CF$_3$ | 5-Cl | 2.29 |
| 44 | H | Me | Et | Me | Me | 3-CF$_3$ | 5-Cl | 2.15 |
| 45 | H | Me | Et | Me | Me | 2-(4-Cl-Ph) | | 2.66 |
| 46 | H | —(CH$_2$)$_4$— | | Me | Me | | 2-Cl | 1.81 |
| 47 | H | —(CH$_2$)$_5$— | | Me | Me | | 2-Cl | 1.96 |
| 48 | H | Me | Et | Me | Me | 2-Et | 4-Cl | 1.98 |
| 49 | H | Me | Et | Me | Me | 2-Cl | 3-Me | 2.01 |
| 50 | H | —(CH$_2$)$_5$— | | Me | Me | 2-Cl | 3-Me | 2.21 |
| 51 | H | Me | nPr | Me | Me | 2-Cl | 3-Me | 2.17 |
| 52 | H | —(CH$_2$)$_4$— | | Me | Me | 2-Cl | 3-Me | 2.05 |
| 53 | H | —(CH$_2$)$_5$— | | Me | Me | 2-iPr | 4-Cl | 2.34 |
| 54 | H | Me | nPr | Me | Me | 2-iPr | 4-Cl | 2.35 |
| 55 | H | —(CH$_2$)$_4$— | | Me | Me | 2-iPr | 4-Cl | 2.22 |
| 56 | H | Me | Et | Me | Me | | 4-Cl | 1.75 |
| 57 | H | Me | Et | Me | Me | | 2-Br | 1.89 |
| 58 | H | Me | nPr | Me | Me | | 2-Br | 2.04 |
| 59 | H | —(CH$_2$)$_5$— | | Me | Me | | 2-Br | 2.06 |
| 60 | H | —(CH$_2$)$_4$— | | Me | Me | | 2-Br | 1.90 |
| 61 | H | Me | Et | Me | Me | | 2-CF$_3$ | 1.98 |
| 62 | H | Me | Et | Me | Me | | 2,3-F$_2$-4-CF$_3$ | 2.31 |
| 63 | H | Me | nPr | Me | Me | | 2,3-F$_2$-4-CF$_3$ | 2.48 |

Preparation Example 64

N-Ethyl-N-methyl-N'-[4-(3-chlorpyridyl-5-oxy)-2,5-xylyl]formamidine—compound of formula (I)

0.50 g (2.19 mmol) of 4-(3-chlorpyridyl-5-oxy]-2,5-xylidine were dissolved in 10 ml of methanol and treated with 0.53 g of a solution of N-ethyl-N-methylformamiddimethylacetal in methanol (77%). The reaction mixture was stirred at 45° C. for 12 h before the solvent was removed in vacuo to yield 620 mg (95% yield, 99% purity) of product; log P (pH 2.3)=1.70. $^1$H NMR δ(ppm) 1.19 (t, $^3$J$_{HH}$=7 Hz, 3H, CH$_3$), 2.10 (s, 3H, CH$_3$), 2.12 (s, 3H, CH$_3$), 2.48 (s, 3H, CH$_3$), 3.04 (s, 3H, NCH$_3$), 3.29 (q, $^3$J$_{HH}$=7 Hz, 2H, NCH$_2$), 6.77 (s, 1H, aryl-H), 7.14 (m, 1H, aryl-H), 7.21 (m, 1H, aryl-H), 7.94 (s, 1H, aryl-H), 8.12 (s, 1H, aryl-H), amidine-H not detected.

Preparation of Starting Material 4-(3-chlorpyridyl-5-oxy)-2,5-xylidine—compound of formula (VII)

2.7 g (10.45 mmol) of 4-(3-chlorpyridyl-5-oxy)-2,5-dimethylnitrobenzene were dissolved in 10 ml of methanol and 10 ml of concentrated hydrochloric acid before 7.01 g (31.36 mmol) of stannous chloride were added. The reaction mixture was refluxed for 4 h, cooled to room temperature and extracted with dichloromethane (2×50 ml). The combined organic layers were dried (MgSO₄), filtered and evaporated to dryness to yield 2.2 g of pure product (92%); log P (pH 2.3)=1.83.

¹H NMR δ(ppm) 2.15 (s, 3H, CH₃), 2.27 (s, 3H, CH₃), 2.58 (s, 3H, CH₃), 4.5 (b, 2H, NH₂), 6.90 (m, 1H, aryl-H), 7.32 (m, 1H, aryl-H), 7.49 (m, 1H, aryl-H), 7.55 (m, 1H, aryl-H), 8.27 (m, 1H, aryl-H).

4-(3-chlorpyridyl-5-oxy)-2,5-dimethylnitrobenzene—compound of formula (IV)

2.00 g (10.78 mmol) of 4-chloro-2,5-dimethylnitrobenzene, 1.29 g (11.86 mmol) of 3-hydroxy-6-methylpyridine and 1.93 g (14.01 mmol) of potassium carbonate were suspended in 10 ml of DMF. The reaction mixture was refluxed for 2 h, cooled down to room temperature, treated with 100 ml of water and 50 ml of a 2N solution of sodium hydroxide in water and extracted with dichloromethane (2×100 ml). The combined organic extracts were dried (MgSO₄), filtered and evaporated to dryness. The crude product was purified by silica gel chromatography eluting with cyclohexane/ethyl acetate to yield the title compound in 94% yield (2.9, 95% purity); log P (pH 2.3)=3.61.

¹H NMR δ(ppm) 2.30 (s, 3H, CH₃), 2.42 (s, 3H, CH₃), 2.58 (s, 3H, CH₃), 6.79 (m, 1H, aryl-H), 7.32 (m, 1H, aryl-H), 7.43 (m, 1H, aryl-H), 8.04 (m, 1H, aryl-H), 8.29 (m, 1H, aryl-H),

TABLE 2

| N° | R¹ | R² | R³ | R⁴ | R⁵ | R⁶ | logP$_a$ |
|----|----|----|----|----|----|----|----------|
| 65 | H  | Me | Et | Me | Me | 2-Me | 0.60 |
| 66 | H  | Me | Et | Me | Me | 6-Me | 1.56 |
| 67 | H  | Me | Et | Me | Me | 3-Cl | 1.82 |

Preparation Example 68

N-Ethyl-N-methyl-N'-[4-(2-ethyl-3-chloropyridyl-4-oxy)-2,5-xylyl]form-amidine—compound of formula (I)

0.20 g (0.72 mmol) of 4-(2-ethyl-3-chloropyridyl-4-oxy)-2,5-xylidine and 5 mg of p-toluene sulfonic acid were refluxed in 20 ml of trimethylformiate for 3 h. The reaction mixture was cooled to room temperature and the solvent was removed in vacuo. The residue was dissolved in 50 ml of dichloromethane and subsequently treated with 0.09 g (1.45 mmol) of N-ethyl-N-methylamine. After stirring at room temperature for 16 h the solvent and unreacted amine was removed in vacuo to give the product in excellent yield (240 mg, 99%) and purity (98%); log P (pH 2.3)=1.47.

¹H NMR δ(ppm) 1.16 (t, ³J$_{HH}$=7 Hz, 3H, CH₃), 1.26 (t, ³J$_{HH}$=7 Hz, 3H, CH₃), 2.01 (s, 3H, CH₃), 2.17 (s, 3H, CH₃), 2.93 (q, ³J$_{HH}$=7 Hz, 2H, CH₂), 2.99 (s, 3H, NCH₃), 3.42 (q, ³J$_{HH}$=7 Hz, 2H, NCH₂), 6.40 (m, 1H, pyridine-H), 6.81 (s, 1H, Ph-H), 6.83 (s, 1H, Ph-H), 7.71 (s, 1H, amidine-H), 8.22 (m, 1H, pyridine-H).

Preparation of Starting Material

4-(2-Ethyl-3-chloropyridyl-4-oxy)-2,5-xylidine—compound of formula (VII)

3.11 g (22.72 mmol) of 4-amino-2,5-dimethylphenol, 4.00 g (22.72 mmol) of 3,4-dichloro-2-ethylpyridine and 5.02 g (36.05 mmol) of potassium carbonate were suspended in 50 ml of DMSO under argon atmosphere. The reaction mixture was stirred at 120° C. for 6 h, cooled down to room temperature, treated with 150 ml of water and 50 ml of a 2N solution of sodium hydroxide in water and extracted with dichloromethane (2×100 ml). The combined organic extracts were dried (MgSO₄), filtered and evaporated to dryness. The crude product was purified by silica gel chromatography eluting with cyclohexane/ethyl acetate to yield the title compound in 59% yield (3.7 g, 97% purity); log P (pH 2.3)=1.66.

¹H NMR δ(ppm) 1.25 (t, ³J$_{HH}$=7 Hz, 3H, CH₃), 1.92 (s, 3H, CH₃), 2.03 (s, 3H, CH₃), 2.91 (q, ³J$_{HH}$=7 Hz, 2H, CH₂), 4.64 (s, 2H, NH₂), 6.37 (m, 1H, pyridine-H), 6.57 (s, 1H, Ph-H), 6.68 (s, 1H, Ph-H), 8.17 (m, 1H, pyridine-H).

TABLE 3

| N° | R¹ | R² | R³ | R⁴ | R⁵ | R⁶ | | logP$_a$ |
|----|----|----|----|----|----|-----|------|------|
| 69 | H | Me | Et | Me | Me | 2-Cl | | 1.45 |
| 70 | H | —(CH₂)₅— | | Me | Me | 2-Cl | | 1.66 |
| 71 | H | —(CH₂)₄— | | Me | Me | 2-Cl | | 1.52 |
| 72 | H | Me | nPr | Me | Me | 2-Cl | | 1.56 |
| 73 | H | Me | Allyl | Me | Me | 2-Et | 3-Cl | 1.51 |
| 74 | H | Me | nPr | Me | Me | 2-Et | 3-Cl | 1.59 |
| 75 | H | —(CH₂)₅— | | Me | Me | 2-Et | 3-Cl | 1.56 |
| 76 | H | —(CH₂)₄— | | Me | Me | 2-Et | 3-Cl | 1.43 |
| 77 | H | Me | Et | Me | Me | 2-CF₃ | | 1.75 |
| 78 | H | Me | nPr | Me | Me | 2-CF₃ | | 1.75 |
| 79 | H | —(CH₂)₅— | | Me | Me | 2-CF₃ | | 1.78 |
| 80 | H | —(CH₂)₄— | | Me | Me | 2-CF₃ | | 1.69 |
| 81 | H | Me | Allyl | Me | Me | 2-Cl | | 1.74 |

Efficacy Example A

In Vivo Preventive Test on *Puccinia recondite f. Sp. tritici* (Wheat Brown Rust)

| Solvent: | 50 parts by weight of n,n-dimethylacetamid |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are inoculated with a spore suspension of *Puccinia recondita* in a 0.1% strength aqueous agar solution. After the spray coating has dried on, the plants are sprayed with the preparation of active compound at the stated rate of application. The plants remain for 24 hours in an incubation cabinet at 20° C. and a relative atmospheric humidity of 100%.

The plants are placed in a greenhouse at a temperature of approximately 20° C. and a relative atmospheric humidity of approximately 80% to promote the development of rust pustules.

The test is evaluated 10 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1; 3; 4; 5; 6; 7; 9; 10; 11; 12; 13; 14; 18; 19; 23, 26; 27; 28; 29; 32; 33; 34; 35; 42; 43; 44; 47; 50; 57; 58; 59; 60; 61; 64; 66; 68; 69; 70; 71; 74; 75; 76; 81.

Efficacy Example B

In Vivo Preventive Test on *Erysiphe gramini* (Powdery Mildew on Barley)

| Solvent: | 50 parts by weight of n,n-dimethylacetamid |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has dried on, the plants are dusted with spores of *Erysiphe graminis f.sp. hordei*.

The plants are placed in a greenhouse at a temperature of approximately 20° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1; 3; 4; 6; 7; 10; 11; 12; 14; 18; 19; 23, 26; 27; 28; 29; 33; 34; 35; 42; 43; 44; 47; 64; 66; 68; 69; 70; 72; 74; 75; 76.

Efficacy Example C

In Vivo Protective Test on *Alternaria solani* (Leaf Spot of Tomato)

| Solvent: | 49 parts by weight of N,N-dimethylformamide |
|---|---|
| Emulsifier: | 1 part by weight of alkylarylpolyglycolether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Alternaria solani*. The plants remain for one day in an incubation cabinet at approximately 20° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control while an efficacy of 100% means that no disease is observed.

In this test, invention related compounds of the following formula revealed an efficacy of 70% or higher at a concentration of 500 ppm of active ingredient: 1; 6; 12; 23; 48; 69.

Efficacy Example D

In Vivo Protective Test on *Podosphaera leucotricha* (Apples)

| Solvent: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 1; 6; 12; 13; 23; 28; 34; 66; 69; 73; 74.

Efficacy Example E

In Vivo Protective Test on *Sphaerotheca fuliginea* (Cucumbers)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protect activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 1; 6; 12; 13; 21; 22; 23; 26; 28; 33; 34; 42; 48; 54; 55; 57; 66; 68; 69; 73; 74; 75.

Efficacy Example F

In Vivo Protective Test on *Uromyces appendiculatus* (Beans)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 10 ppm of active ingredient: 48; 50; 54; 55; 57

The invention claimed is:

1. A phenyl-amidine derivative of formula (I):

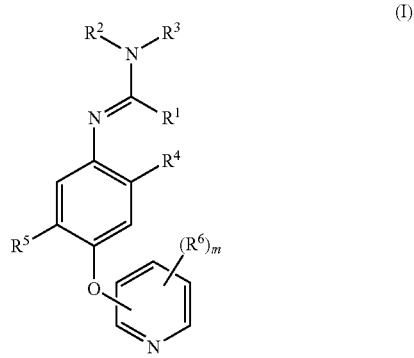

wherein
$R^1$ represents H, a substituted or non substituted $C_1$-$C_{12}$-alkyl, a substituted or non substituted $C_2$-$C_{12}$-alkenyl, a substituted or non substituted $C_2$-$C_{12}$-alkynyl, SH or a substituted or non substituted S—$C_1$-$C_{12}$-alkyl;
$R^2$ represents a substituted or non substituted $C_1$-$C_{12}$-alkyl;
$R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or
$R^1$ and $R^2$, $R^1$ and $R^3$ or $R^2$ and $R^3$ can form together a substituted or non substituted 5 to 7-membered heterocycle;
$R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
$R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
m represents 1, 2, 3 or 4;
$R^6$ represents H, halogen, cyano, substituted or non substituted phenoxy, substituted or non substituted phenyl, substituted or non substituted $C_1$-$C_{12}$-alkyl, or halogeno-$C_1$-$C_{12}$-alkyl, $NR^7R^8$, $OR^7$, $SR^7$, trialkysilyl, $COOR^7$, $C(R^7)$=$NOR^8$;
$R^7$, $R^8$ represent H, substituted or non substituted $C_1$-$C_{12}$-alkyl, aryl;
$R^7$ and $R^8$ may form a substituted or non substituted, saturated or non saturated 5- to 7-membered heterocycle;
as well as a salt; N oxide, metallic complex, metalloidic complex and/or optically active or geometric isomer thereof.

2. A compound of formula (I) according to claim 1 wherein
$R^1$ represents H, $C_1$-$C_{12}$-alkyl or SH; or
$R^2$ represents methyl or ethyl; or
$R^3$ represents $C_2$-$C_{12}$-alkyl, $C_2$-$C_{12}$-alkenyl or $C_3$-$C_6$-cycloalkyl; or
$R^2$ and $R^3$ can form together a substituted or non substituted 5- to 7-membered heterocycle; or
$R^4$ represents $C_1$-$C_{12}$-alkyl or a halogen atom; or
$R^5$ represents a $C_1$-$C_{12}$-alkyl or a halogen atom; or $R^6$ represents H, a halogen atom, cyano, substituted or non substituted $C_1$-$C_{12}$-alkyl, or halogeno-$C_1$-$C_{12}$-alkyl, $NR^7R^8$, $OR^7$, $SR^7$, $COOR^7$; or $R^7$ and $R^8$ independently represent H, methyl, ethyl, substituted phenyl; or $R^7$ and $R^8$ may form a substituted or non substituted, saturated or non saturated 5- to 7-membered heterocycle;

as well as a salt, N-oxide, metallic complex, metalloidic complex and/or optically active or geometric isomer thereof.

3. A compound of formula (I) according to claim 1 wherein $R^1$ represents $C_1$-$C_{12}$-alkyl; or $R^3$ represents a non substituted $C_2$-$C_4$-alkyl, $C_3$-$C_4$-alkenyl or cyclopropyl; or $R^2$ and $R^3$ can form together a 6-membered heterocycle; or $R^4$ represents a non substituted $C_1$-$C_{12}$-alkyl or a chlorine atom; or $R^5$ represents a non substituted $C_1$-$C_{12}$-alkyl or a chlorine atom; or $R^7$ and $R^8$ may form a piperidinyl or a morpholinyl;

as well as a salt, N-oxide, metallic complex, metalloidic complex and/or optically active or geometric isomer thereof.

4. A compound of formula (I) according to claim 1 wherein $R^1$ represents methyl or ethyl; or $R^3$ represents ethyl, n-propyl, i-propyl, propenyl or allyl; or $R^2$ and $R^3$ can form together a piperidinyl or a pyrrolidinyl; or $R^4$ represents methyl or ethyl; or $R^5$ represents methyl or ethyl;

as well as a salt, N-oxide, metallic complex, metalloidic complex and/or optically active or geometric isomer thereof.

5. A compound of formula (I) according to claim 1 wherein $R^2$ and $R^3$ form together a bis-alkylated-pyrrolidinyl, as well as a salt, N-oxide, metallic complex, metalloidic complex and/or optically active or geometric isomer thereof.

6. A compound of formula (I) according to claim 5 wherein $R^2$ and $R^3$ form together a bis-methyl-pyrrolidinyl, as well as a salt, N-oxide, metallic complex, metalloidic complex and/or optically active or geometric isomer thereof.

7. A process for the preparation of a compound of formula (I) according to claim 1 comprising the following steps:

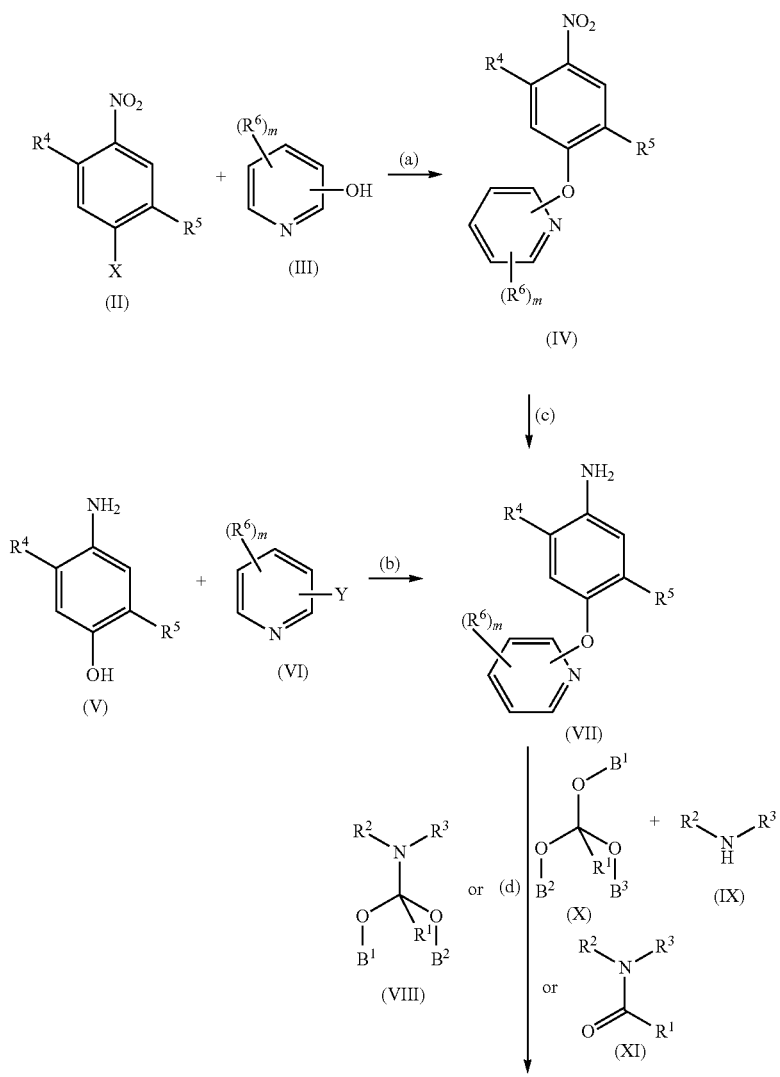

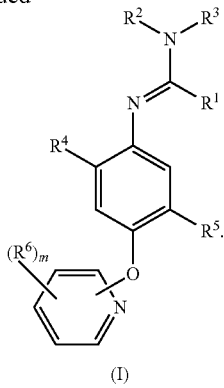

(I)

8. A method for controlling phytopathogenic fungi of crops, comprising applying an agronomically effective and substantially non-phytotoxic quantity of a compound according to claim 1 to soil where a plant grows or is capable of growing, and/or to leaves and/or fruit of a plant or to a seed of a plant.

9. A compound of formula (I) according to claim 1 wherein
$R^1$ represents H, or a substituted or non substituted $C_1$-$C_{12}$-alkyl;
$R^2$, $R^3$, $R^4$, and $R^5$ represent, independently, a substituted or non substituted $C_1$-$C_{12}$-alkyl;
$R^6$ represents H, halogen, substituted or non substituted $C_1$-$C_{12}$-alkyl, or halogeno-$C_1$-$C_{12}$-alkyl; and
m represents 1 or 2;
as well as a salt, N-oxide, metallic complex, metalloidic complex and/or optically active or geometric isomer thereof.

10. A compound of formula (I) according to claim 1 wherein
$R^1$ represents H;
$R^2$, $R^3$, $R^4$, and $R^5$ represent, independently, methyl, ethyl, n-propyl, or i-propyl;
$R^6$ represents bromo, chloro, methyl, ethyl, i-propyl, or —$CF_3$; and
m represents 1 or 2;
as well as a salt, N-oxide, metallic complex, metalloidic complex and/or optically active or geometric isomer thereof.

11. A compound of formula (I) according to claim 1 wherein
$R^1$ represents H;
$R^2$, $R^4$, and $R^5$ represent methyl;
$R^3$ represents ethyl, n-propyl, or i-propyl;
$R^6$ represents: at position 2, H, bromo, chloro, methyl, ethyl, or i-propyl; at position 3, H, chloro, or —$CF_3$; at position 4, H, chloro, or —$CF_3$; at position 5, H or chloro; at position 6, H or methyl; or combinations thereof; and
m represents 1 or 2;
as well as a salt, N-oxide, metallic complex, metalloidic complex and/or optically active or geometric isomer thereof.

12. A compound of formula (I) according to claim 1 wherein
$R^1$ represents H;
$R^2$, $R^4$, and $R^5$ represent methyl;
$R^3$ represents ethyl, n-propyl, or i-propyl;
$R^6$ represents: 2-chloro-4-trifluoromethyl; 2-chloro-3-trifluoromethyl; 2-methyl-4-chloro; 2-ethyl-3-chloro; 2-ethyl-4-chloro; 2-isopropyl-4-chloro; 3-chloro-5-chloro; 2-chloro; 2-bromo; or 6-methyl; and
m represents 1 or 2;
as well as a salt, N-oxide, metallic complex, metalloidic complex and/or optically active or geometric isomer thereof.

13. A compound of formula (I) according to claim 1 wherein
$R^1$ represents H;
$R^2$, $R^4$, and $R^5$ represent methyl;
$R^3$ represents ethyl;
$R^6$ represents 2-bromo; and
m represents 1;
as well as a salt, N-oxide, metallic complex, metalloidic complex and/or optically active or geometric isomer thereof.

* * * * *